US005662901A

United States Patent [19]

Tobey, Jr. et al.

[11] Patent Number: 5,662,901

[45] Date of Patent: Sep. 2, 1997

[54] ENZYMATIC GRAIN CONDITIONER AND METHODS OF USING IT

[75] Inventors: James F. Tobey, Jr., Roanoke, Va.; J. Stanley McGee, Longmont, Colo.; Charles W. Cobb, Hereford, Tex.; William Cortner, Maysville, Mo.

[73] Assignees: Loveland Industries, Inc., Greeley, Colo.; George A. Jeffreys & Co., Salem, Va.; Creative Research Laboratories, Inc., Wisner, Nebr.

[21] Appl. No.: 294,087

[22] Filed: Aug. 22, 1994

Related U.S. Application Data

[62] Division of Ser. No. 544,022, Jun. 26, 1990, which is a continuation of Ser. No. 407,726, Sep. 14, 1989, abandoned, which is a continuation of Ser. No. 76,114, Jul. 21, 1987, abandoned.

[51] Int. Cl.$^6$ .......................... A61K 38/54; A61K 38/47; C12N 9/14; A23B 7/10
[52] U.S. Cl. .................. 424/94.2; 424/94.6; 424/94.61; 424/94.63; 435/195; 435/198; 435/200; 435/201; 435/202; 435/203; 435/204; 435/209; 435/210; 435/219; 426/53; 426/54; 426/63
[58] Field of Search .................. 424/94.2, 94.6, 424/94.61, 94.63; 435/195, 196, 200, 201, 202, 203, 204, 209, 210, 219; 426/53, 54, 63

[56] References Cited

U.S. PATENT DOCUMENTS

| | | | |
|---|---|---|---|
| 1,477,964 | 12/1923 | Laughlin | 426/64 |
| 1,615,024 | 1/1927 | Mabee | 426/53 |
| 1,685,004 | 9/1928 | Muslin | 426/53 |
| 2,322,516 | 6/1943 | Horvath | 426/53 |
| 2,450,318 | 9/1948 | Wagamon | 426/8 |
| 2,452,534 | 10/1948 | Jeffreys | 426/18 |
| 2,505,360 | 4/1950 | Jeffreys | 426/18 |
| 2,700,611 | 1/1955 | Jeffreys | 426/18 |
| 2,878,123 | 3/1959 | Beuk et al. | 424/94.21 |
| 2,906,621 | 9/1959 | Catron | 424/94.66 |
| 2,988,448 | 6/1961 | Hollenbeck | 424/94.2 |
| 2,988,449 | 6/1961 | Hollenbeck | 424/94.2 |
| 3,151,983 | 10/1964 | Ely et al. | 424/114 |
| 3,455,696 | 7/1969 | Ukita et al. | 426/31 |
| 3,674,644 | 7/1972 | Yokotsuka | 435/223 |
| 3,861,294 | 1/1975 | Coldren | 99/516 |
| 3,868,448 | 2/1975 | Hahn et al. | 424/94.62 |
| 3,880,742 | 4/1975 | James et al. | 435/200 |
| 3,962,479 | 6/1976 | Coldren | 426/532 |
| 4,035,516 | 7/1977 | Jungvid | 426/53 |
| 4,044,156 | 8/1977 | Diner et al. | 426/53 |
| 4,062,732 | 12/1977 | Lehmann et al. | 426/53 |
| 4,073,884 | 2/1978 | Hartdegen et al. | 424/94.62 |
| 4,100,151 | 7/1978 | Adler-Nissen | 424/94.62 |
| 4,208,433 | 6/1980 | Barham et al. | 426/69 |
| 4,218,437 | 8/1980 | Hiller | 424/53 |
| 4,225,584 | 9/1980 | Hiller | 424/53 |
| 4,235,878 | 11/1980 | Hiller | 424/53 |
| 4,235,879 | 11/1980 | Hiller | 424/94.66 |
| 4,235,880 | 11/1980 | Hiller | 424/94.66 |
| 4,239,750 | 12/1980 | Hiller | 424/94.66 |
| 4,247,561 | 1/1981 | Nelson | 426/53 |
| 4,259,358 | 3/1981 | Duthie | 426/46 |
| 4,508,029 | 4/1985 | Malone | 99/516 |
| 4,540,585 | 9/1985 | Priegnitz | 426/28 |
| 4,582,708 | 4/1986 | Tipton et al. | 426/62 |

FOREIGN PATENT DOCUMENTS

| | | |
|---|---|---|
| 1316226 | 8/1972 | United Kingdom . |
| 212745 | 6/1976 | United Kingdom . |

OTHER PUBLICATIONS

Albin, "What's New in Processing Technique for Grain Sorghum," Seventh Biennial Grain Sorghum Research and Utilization Conference, Lubbock, Texas, Mar. 3, 1971.

Anderson et al., "The Effects of Commercial Grain Conditioners, Fungal Enzyme Preparations or Sodium Hydroxide on Wetting Rate and in situ Digestibility of Corn and Grain Sorghum," Annual Meeting of the Southern Section, American Society of Animal Science, Feb. 7–10, 1982.

Berkeley et al., *Microbial Polysacchandes and Polysaccharases*, 1979, Society for General Microbiology, New York, NY, pp. 278–279, 302–303, 380–389.

Brown, "Enzymology may lead to new feed industry technology," *Feedstuffs*, p. 21, May 11, 1987.

Hoefelmann et al., "Isolation, purification and characterization of lipase isoenzymes from technical *Aspergillus niger* enzyme." J. Food Sci. 50(6), pp. 1721–1725, 1731; 1985.

Loginova et al., "Biosynthesis of cellulytic enzymes and xylanuse during submerged cultivation of the fungus *Aspergillus terrus* 17P," Prikl Biokhim Mikrobiol 14(4), pp. 485–493, 1978.

McEllhiney, "The Cost of Grain Processing," *Feed Management* (1986).

(List continued on next page.)

*Primary Examiner*—Blaine Lankford
*Attorney, Agent, or Firm*—Carol W. Burton; Holland & Hart LLP

[57] ABSTRACT

The invention comprises two grain conditioners. The first grain conditioner, which is suitable for use on all grains, comprises a pectinase, a protease, a beta-glucanase and an amylase. The second grain conditioner, which is designed for use on easier-to-digest grains, comprises a pectinase, a beta-glucanase, an amylase and a hemicellulase. The invention also comprises animal feeds which comprise a grain which has been conditioned with one of the grain conditioners of the invention designed to be effective on that grain and methods of increasing the weight gain and feed utilization efficiency of an animal comprising feeding the novel animal feeds of the invention to the animal. The invention further comprises a method of conditioning a grain which comprises providing the grain, contacting the grain with one of the grain conditioners of the invention designed to be effective on that grain and incubating the grain and grain conditioner together for at least about 30 minutes. Finally, there is also provided another method of conditioning a grain comprising providing the grain, scarifying the grain, contacting the grain with one of the grain conditioners of the invention designed to be effective on that grain and incubating the grain and grain conditioner for at least about 30 minutes.

20 Claims, No Drawings

OTHER PUBLICATIONS

McLeod et al., "Effects of Added Moisture, Or Added Moisture Plus Heat On Utilization Of Grain sorghum", Agricultural Sciences Technical Report No. T-5-213, *Animal Science Research Report* 1986 (Texas Tech University).

*National Research Council, Food Chemicals Codex*, pp. 479-482, 485-486, 490-491, 495-498 (3rd ed., National Academy Press, 1981).

*Proceedings Feed Grains Utilization Symposium (For Feedlot Cattle)*, Sep. 20, 1984.

Richardson et al., "Chemical Grain Conditioners," *Ninth Annual Texas Beef Conference Proceedings*, Apr. 16, 1981.

ENZYMATIC GRAIN CONDITIONER AND METHODS OF USING IT

RELATED APPLICATIONS

This application is a divisional application of pending U.S. patent application Ser. No. 07/544,022 filed Jun. 26, 1990, a continuation of U.S. patent application Ser. No. 07/407,726 filed Sep. 14, 1989 and now abandoned, a continuation of U.S. patent Ser. No. 07/076,114 filed Jul. 21, 1987 and now abandoned.

BACKGROUND OF THE INVENTION

There is a continuing need for methods and products which increase weight gain and feed utilization efficiency in animals. For animals fed diets containing grain, these goals can be achieved by increasing the availability to the animal of the starch, protein and other nutrients found in the grain. The availability of these nutrients can be increased by breaking open the outer coating of the grain and by enlarging the surface area of the grain so that the enzymes and bacteria in the digestive tract of the animal can more easily penetrate the grain and can have access to more of the grain. Weight gain and feed utilization efficiency can be further improved by increasing the moisture content of the grain which also makes it easier for the enzymes and bacteria in the digestive tract to penetrate the grain. Also, the digestive enzymes cannot work until a certain level of moisture in the grain is achieved.

Several techniques are known for processing grains which serve these purposes. For instance, grain can be ground or rolled thereby breaking open the outer coating of the grain and enlarging its surface area. The grain can be soaked or sprayed with water before or after the rolling or grinding to increase its moisture content. To further increase the moisture content, grain conditioners can be added to the water. Grain conditioners are preparations that increase penetration of moisture into the grain. They contain either surfactants, acids or bases. Instead of soaking or spraying the grain with water, early-harvested grain that naturally has a higher moisture content may be used. Other methods of processing grain include steam rolling, steam flaking, popping, exploding and mechanically scarifying.

The mechanical scarification of grains is described in U.S. Pat. Nos. 3,962,479 and 3,861,294. The method described in these patents comprises wetting the exterior of the kernels of grain so that the husks separate partially from the interior portion of the grain in the form of blisters. Next, the blisters are perforated. After perforation of the blisters, the grain may be wetted with water. Feed supplements which are soluble in water may be mixed with the water used to wet the grain. The patents teach that the absorption of water by the grain activates the naturally-occurring enzymes in the grain and that these enzymes co-act with the water to convert or liquify the starch which, in turn, allows the animals to assimilate a greater quantity of the nutrients contained in the grain.

The addition of enzymes to animal feeds is also known to increase feed utilization efficiency and weight gain. For instance, U.S. Pat. No. 2,906,621 (Catron) describes the use of a combination of amylolytic and proteolytic enzymes as an additive in animal feeds. In particular, Catron teaches the use of enzyme mixtures having both proteolytic and amylolytic activities which are obtained from various strains of *Aspergillus, Rhizopus* and Bacillus. Catron also teaches that lipolytic and cellulolytic enzymes may be added to the animal feeds along with the amylolytic and proteolytic enzymes. However, Catron teaches the use of these enzyme only for baby animals whose enzyme systems are incomplete.

U.S. Pat. No. 3,151,983 (Ely et al.) teaches that a feed supplement comprising a mixture of a material prepared by fermenting wet wheat bran using *Aspergillus orizae* and a material prepared by fermenting wet wheat bran using *Bacillus subtilis* results in both increased efficiency of feed utilization and weight gain in animals fed feeds containing barley which are supplemented with these materials. The increase in efficiency of feed utilization is disclosed to be due to the presence of the proteolytic and amylolytic enzymes in the two fermented materials, but the increase in growth response is believed to be due to an unknown, nonenzymatic growth factor.

U.S. Pat. No. 3,880,742 (James et al.) discloses the incorporation of a thermostable beta-glucanase into animal feeds containing barley to degrade the barley beta-glucan. James et al. teaches that the beta-glucanase can be added as a fermentation extract of *Penicillum emersonii* and that the fermentation extract also typically contains cellulase and alpha-amylase. The patent teaches that liquid beta-glucanase-containing fermentation extract may be sprayed onto animal feed pellets containing barley or that the enzyme in dry form or which has been absorbed onto an absorbent solid (such as ground wheat or barley) and dried can be incorporated into the feed mix containing barley before it is pelleted. Finally, James et al. teaches that the use of the beta-glucanase in animal feeds containing barley increases the nutritional value of the feed by promoting degradation of the beta-glucan content of barley and causes increased weight gain.

U.S. Pat. No. 4,259,358 (Duthie) teaches treating a slurry of legumes under controlled conditions of time, temperature and pH with a variety of enzymes. The resultant enzyme-digested product can be fed to young animals and certain older animals such as hogs, horses, cats, dogs and humans. Duthie discloses that amylase and amyloglucosidase can be used to digest the starch in the legumes and that proteases, cellulases, hemicellulases and pectinases may be employed to digest, respectively, protein, cellulose, hemicellulose and pectin. The Duthie patent does not teach, and specifically disclaims, the use of enzymes on cereal grains such as wheat, oats, barley and milo.

U.S. Pat. Nos. 2,988,448 (the '448 patent) and 2,988,449 disclose that using diastatic barley malt as an enzyme supplement for animals feeds containing barley and other fibrous grains results in increased weight gain and feeding efficiency. Both of the patents attribute the increases to the cytolytic enzymes (cytases, gumases (beta-glucanases) and beta-polyglucosidases) present in the barley malt. Further, the '448 patent teaches that a combination of diastatic barley malt and fungal enzyme preparations act synergistically in increasing the value of barley and other fibrous grains in animal feeds. The mechanism of the action of the enzyme preparations is believed to be due to the action of cytases in these preparations which degrade the non-starch carbohydrate material commonly referred to as gums (beta-glucan).

U.S. Pat. No. 4,208,433 (Barham et al.) discloses a method for the absorption of solids by the tissues of whole grain seeds comprising contacting the whole grain seed with a mixture of a solid material (such as an enzyme) and an oleaginous vehicle (such as vegetable oil) and maintaining contact until the mixture has been absorbed by the grain. Barham et al. disclose that the absorption of proteolytic enzymes into the seed endosperm in this manner causes the degradation of the protein matrix under appropriate superimposed moisture and temperature conditions and that the degradation of the starch-protein matrix enhances the general availability of starch and protein to the animal. The patent also discloses that the absorption of amylolytic enzymes would cause the partial digestion of the starch which would be advantageous to the animal.

Numerous patents disclose the use of proteolytic enzymes as supplements in animal feeds. These include U.S. Pat. Nos. 2,450,318, 2,878,123, 3,674,644, 4,062,732, 4,073,884, 4,235,878, 4,235,879, 4,235,880, 4,239,750, 4,218,437 and 4,225,584.

Several patents disclose the use of micro-organisms or ferments of microorganisms (containing or capable of producing enzymes) as feed supplements. These are U.S. Pat. Nos. 1,615,024, 1,685,004, 2,450,318, 2,452,534, 2,700,611, 3,455,696, 4,035,516 and 4,582,708.

BRIEF DESCRIPTION OF THE INVENTION

According to one aspect of the invention there is provided a novel grain conditioner useful for conditioning all grains, including hard-to-digest grains, comprising a pectinase, a protease, a beta-glucanase and an amylase. There is also provided a second novel grain conditioner for use on easier-to-digest grains which comprises a pectinase, a beta-glucanase, an amylase and a hemicellulase.

As used herein, the term "hard-to-digest" is used to refer to those grains which are utilized less efficiently by animals. Such grains are also said to have a low feeding value and low nutritional value. The hard-to-digest grains include barley, milo (sorghum), rye and oats.

Grains which are "easier-to-digest" are those which are utilized more efficiently, have a higher feeding value and higher nutritional value than the hard-to-digest grains. However, the easier-to-digest grains can still benefit from treatments which make more of their nutrients available to animals. The easier-to-digest grains include corn and wheat.

The hard-to-digest grains are utilized less efficiently by animals because of differences in structure and chemical composition of these grains as compared to the easier-to-digest grains. The following factors are important in determining whether a grain should be classified as a hard-to-digest or an easier-to-digest grain:

1. Amount of beta-glucan contained in the grain. For instance, barley has a very high level of beta-glucan and is a hard-to-digest grain.
2. Amount of fiber (cellulose and hemicellulose) contained in the grain. For instance, oats has a very high level of cellulose and is a hard-to-digest grain.
3. Shape and size of the-starch granules. For example, the starch granules in milo (a hard-to-digest grain) are smaller than the starch granules in corn easier-to-digest grain). Also, the starch granules in milo are spherical and more irregular in shape than the starch granules in corn which are hexagonal and uniform in shape.
4. The degree of shrouding of the starch granules. For instance, essentially all of the starch granules of milo are shrouded or embedded in the protein matrix or coating of the grain, whereas corn has a substantial percentage of free starch granules.
5. The density of packing of the starch granules. For example, the starch granules of milo are more tightly packed than those of corn.
6. The solubility of the protein contained in the grain. For instance, the protein contained in milo and rye is much less soluble than the protein contained in corn.
7. The degree of complexation of the protein with cellulose and hemicellulose in the grain. The greater the degree of complexation, the harder the grain is to digest.

It is not possible to assign numerical limits to these factors so as to be able to distinguish hard-to-digest from easier-to-digest grains since there can be considerable variation even for the same grain from year to year or region to region and between varieties of the same grain. Also, the classification of the grain as hard-to-digest or easier-to-digest must be considered in the context of the animal consuming the grain. For instance, the level of cellulose and hemicellulose does not substantially affect digestibility of grains by ruminants, whereas it does have a substantial effect on the digestibility of grains by non-ruminants.

However, a side-by-side comparison of any grain not specifically mentioned herein with those which are mentioned, using tests known to those skilled in the art to determine, e.g., feed utilization efficiency, would make it possible to assign a grain either to the hard-to-digest or the easier-to-digest category for a given animal. Moreover, those skilled in the art are generally familiar with which grains fall into each of these two categories for different animals.

Bacterial and fungal enzymes are preferred for practicing the invention. To obtain the enzymes, appropriate microorganisms, as described below, are cultured using conventional techniques. Each microorganism is cultured separately, and the enzymes produced during the culture period are blended to produce the enzymatic grain conditioners of the invention. Alternatively, suitable enzymes can be purchased commercially. Crude fermentation products, partially purified fermentation products (microorganisms and non-enzymatically active solids removed) and purified enzymes may be used to prepare the grain conditioners of the invention.

According to the invention, there are further provided: (1) a method of conditioning a grain comprising contacting the grain with one of the enzymatic grain conditioners of the invention designed to be effective on that grain and incubating the grain and grain conditioner together for at least about 30 minutes; and (2) a method of conditioning a grain comprising scarifying the grain, contacting the scarified grain with one of the enzymatic grain conditioners of the invention designed to be effective on that grain and incubating the grain and grain conditioner together for at least about 30 minutes. Although the grain conditioners of the invention improve the feeding value of whole grains, the outer coating of the grain is preferably broken open before the grain is contacted with the grain conditioners of the invention. Even more preferably, the grain will have been processed to enlarge the surface area of the grain (such as by grinding or rolling) before it is contacted with the grain conditioner.

Grains contacted with the enzymatic grain conditioners of the invention show increased carbohydrate availability and dry matter digestibility in in vitro tests. Also, animals fed feeds containing grains treated with the grain conditioners of the invention show improved weight gains and feed utilization efficiency. Accordingly, there are provided according to the invention a novel animal feed comprising a grain treated with a grain conditioner of the invention designed to be effective on that grain and a method of increasing the weight gain and feed utilization efficiency of animals comprising feeding the animals the novel animal feeds of the invention.

DETAILED DESCRIPTION OF THE PRESENTLY PREFERRED EMBODIMENTS

Enzymes Useful In Practicing The Invention

1. Pectinases

The pectin carbohydrates which occur in grains are composed of polymers of galacturonic acid (also referred to as pectic acid). Pectin is the methyl ester of pectic acid. The degree of methyl esterification of pectic acid varies with the type of plant, the time of harvest and the growth conditions experienced by the plant.

There are two types of pectinases: depolymerizing pectic enzymes and pectinesterases. Depolymerizing enzymes act either mainly on pectin (polymethylgalacturonase and pectin lyase) or mainly on pectic acid (polygalacturonase and pectate lyase). Each of the types of depolymerizing enzymes may further be either exo- or endo-acting.

In practicing the invention, it is preferable to use a combination of pectinases which can act broadly on the pectic acid, pectin and compounds of similar structure, known generally as "pectic substances," which are present in the outer coating of grains and are often enmeshed with other grain constituents. Thus, a combination of a pectinesterase and depolymerizing pectic enzymes which act on both pectin and pectic acid is preferred. Further, most preferably, both exo- and endo-acting depolymerizing pectic enzymes are used.

Depolymerizing pectic enzymes suitable for use in the invention are produced by members of the *Aspergillus oryzae/soyae* and the *Aspergillus niger* groups of fungi. Also suitable for use in the invention are the depolymerizing pectic enzymes produced by the various species of Rhizopus. In particular, a combination of the depolymerizing pectic enzymes produced by *A. niger* and *R. oryzae* are preferred in the practice of the invention.

Pectinesterases and pectate lyases useful in practicing the invention can be obtained by appropriately culturing various species of the genus Bacillus. Preferred are *B. subtilis* and *B. licheniformis*.

2. Proteases

Any known protease is suitable for use in the invention. However, the protease selected must be capable of operating in the grain and under the conditions of the grain treatment. These conditions cannot always be predicted. For instance, the pH of grains varies depending on the type of grain, the region in which it is grown and the time of harvest. Also, barley contains an inhibitor of alkaline proteases. Thus, especially preferred is a combination of alkaline, neutral and acidic proteases having broad specificity.

Proteases suitable for practicing the invention include those that can be obtained by culturing *A. niger, A. oryzae, Rhizopus spp., B. subtilis, B. licheniformis* and other species of the genus Bacillus. Preferred is a combination of the proteases produced by *A. oryzae* (acid protease) and either *B. subtilis* or *B. licheniformis* (sources of neutral and alkaline proteases).

3. Beta-Glucanase

Beta-glucan is a linear polymer of glucose that is linked by beta-1,4 and beta-1,3 bonds. Beta-glucan is present in all grains, but the cell walls of barley contain particularly large amounts of beta-glucan.

Beta-glucan is degraded by beta-glucanase (1,3-1,4-beta-D-glucan-4-glucanohydrolase). A combination of the beta-glucanases produced by *A. oryzae* and *B. subtilis* is preferred for use in the invention. The beta-glucanase produced by *A. oryzae* breaks down both beta-1,4 and beta-1,3 bonds, and *B. subtilis* produces beta-glucanase in larger quantities than other microorganisms.

4. Amylases

Grains, of course, contain considerable amounts of starch, and starch is digested by amylases. Amylases useful in practicing the invention may be obtained by culturing *A. oryzae, B. subtilis, B. licheniformis, B. stearothermophilus, Rhizopus oryzae* or other species of Aspergillus. Especially preferred is a combination of the amylases produced by *B. subtilis* and *A. oryzae*.

5. Hemicellulase

Hemicellulase degrades the hemicellulose found in grains and plant cell walls. Hemicellulases useful in practicing the invention can be obtained by culturing *B. subtilis, A. oryzae* and *A. niger*. Especially preferred is a combination of the hemicellulases produced by *B. subtillis* and *A. oryzae*.

All of the microorganisms referred to above as sources of enzymes for use in the invention are well-known and widely-available.

Culturing The Microorganisms

As stated above, the microorganisms can be cultured using any conventional method. For instance, techniques such as those set forth in the following examples may be used.

EXAMPLE 1

*B. subtills* was cultured with shaking for 30–36 hours at 30°–35° C. in an aqueous medium containing 0.5% beef extract, 0.4% beef peptone, 0.2% magnesium sulfate, 0.1% calcium chloride, 0.01% manganese chloride and 0.1% autolysed yeast extract in water (hereinafter Medium A).

At the end of this time, the culture was actively growing and was inoculated into a stainless steel fermenter containing 2000 liters of an aqueous medium containing 1% soybean flour, 3.0% corn starch, 0.1% magnesium sulfate 0.1% calcium chloride and 0.01% manganese chloride (hereinafter Medium B). Vigorous agitation was applied, and sterile filtered air was blown into the fermenter.

The fermentation was allowed to proceed for 48 hours while the temperature was maintained at 35° C. The pH of the medium was initially 7.0 and, after 48 hours, was 7.8. At the end of the fermentation period, the temperature was reduced to 4° C., and the calcium chloride content of the ferment was adjusted to 0.06M.

Next, the fermentation product was passed through a continuous centrifuge where most of the bacterial cells and other solids were removed. The liquid was then concentrated under vacuum evaporation at temperatures not exceeding 45° C. After concentration, the liquid was cooled once again to 4° C. and passed through a filter press to remove the remainder of the bacterial cells and solids.

EXAMPLE 2

*B. licheniformis* was cultured and fermented as described above in Example 1, and the liquid from the fermentation was separated from the microorganisms and other solids and further treated as also described in that example.

EXAMPLE 3

*B. stearothermophilus* was cultured and fermented as described above in Example 1, and the liquid from the fermentation was separated from the microorganisms and other solids and further treated as also described in that example.

EXAMPLE 4

A. oryzae was cultured in Medium A as described in Example 1, except that the Medium A was supplemented with 2% Difco agar and sufficient acetic acid/acetate buffer to lower the pH to 5.6. The A. Oryzae was cultured in this modified Medium A until spores were formed, at which time the spores were rinsed off the semi-solid medium. The resultant spore suspension was used to inoculate the fermenter. Fermentation was performed as described above in Example 1, except that 3% corn steep liquor was substituted for the corn starch in Medium B and the pH was kept at 5.2. The liquid from the fermentation was separated from the microorganisms and other solids and further treated as described in Example 1.

EXAMPLE 5

A. niger was cultured as described above in Example 4. The liquid from the fermentation was separated from the microorganisms and other solids and further treated as described in that example.

EXAMPLE 6

R. oryzae was cultured as described above in Example 4. The liquid from the fermentation was separated from the microorganisms and other solids and further treated as described in that example.

EXAMPLE 7

A. oryzae was cultured on a semi-solid (40–70% water) medium as described in U.S. Pat. No. 2,505,560, which is incorporated herein by reference. After culturing was complete, the enzymes were extracted using countercurrent extraction with water at 4°–25° C., passage time 45–60 minutes. The liquid from this extraction procedure was separated from the microorganisms and other solids and further treated as described in Example 1.

EXAMPLE 8

A. niger was cultured as described in Example 7, and the liquid containing the enzymes was separated from the microorganisms and other solids and further treated as also described in that example.

EXAMPLE 9

B. subtilis was cultured as described above in Example 7, and the liquid from the fermentation was separated from the microorganisms and other solids and further treated as described in that example.

EXAMPLE 10

B. licheniformis was cultured as described in Example 7, and the liquid containing the enzymes was separated from the microorganisms and other solids and further treated as also described in that example.

EXAMPLE 11

B. stearothermophilus was cultured as described in Example 7, and the liquid containing the enzymes was separated from the microorganisms and other solids and further treated as also described in that example.

EXAMPLE 12

R. oryzae was cultured as described in Example 7, and the liquid containing the enzymes was separated from the microorganisms and other solids and further treated as also described in that example.

EXAMPLE 13

A culture and fermentation was performed as described in any of Examples 1–12. Then, sufficient ammonium sulfate was added to the resultant liquid so that the concentration of ammonium sulfate reached 70–75% of saturation. The liquid was then held at 4° C. for 5 hours to precipitate the enzymes. The resultant precipitate was separated by centrifugation, washed with a cold isopropyl alcohol-acetone mixture and dried under vacuum.

The fermentation product obtained using any of the procedures of Examples 1–13 is a partially purified (microorganisms and non-enzymatically active solids removed) mixture of enzymes. These mixtures may be further purified by known conventional techniques. Thus, liquids or powders containing a single enzyme can be obtained. These purified enzymes can be used to prepare the grain conditioners of the invention, but partially purified mixtures of enzymes (such as those prepared in Examples 1–13) are preferred in practicing the invention because of the lower cost of their preparation compared to purified enzymes. Crude fermentation products from which the microorganisms and solids have not been removed may also be used in practicing the invention, but it is more difficult to process such crude fermentation products as compared to partially purified enzyme mixtures or purified enzymes.

Enzyme Assays

To prepare the grain conditioners of the invention, the enzyme activity of the crude fermentation products, partially purified enzyme mixtures or purified enzymes which are to be used in the grain conditioners is first determined using the following assays.

a. Assay For Amylase

Alpha-amylase from fungal sources was assayed as described in *Food And Nutrition Board, National Research Council, Food Chemicals Codex* 479-82 (3rd ed. 1981) (hereinafter *Food Chemicals Codex*), which is incorporated herein by reference. Briefly, the assay is based on the time required to obtain a standard degree of hydrolysis of a starch solution (beta-limit dextrin prepared from Baker Reagent Grade soluble potato starch) at 30° C., pH 4.8. The degree of hydrolysis is determined by comparing the iodine color of the iodine/starch hydrolysate complex with that of a standard. One unit of fungal alpha-amylase activity (an SKB) is defined as that quantity of alpha-amylase that will hydrolyze beta-limit dextrin at the rate of one gram per hour under the conditions of the assay.

Alpha-amylase from bacterial sources was assayed as described in *Food Chemicals Codex* 482, which is incorporated herein by reference. Briefly, the assay is performed in the same manner as the assay of fungal alpha-amylase activity, except that the pH is 6.6 rather than 4.8. One bacterial alpha-amylase unit (BAU) of activity is defined as that quantity of enzyme that will dextrinize 1 mg starch per minute under the assay conditions.

b. Assay For Beta-glucanase

Beta-glucanase was assayed as described in *Food Chemicals Codex* 485, which is incorporated herein by reference. Briefly, the assay is based on a 15-minute hydrolysis of lichenin substrate at 40° C., pH 6.5. The increase in reducing power due to liberated reducing groups is measured by the neocuproine method. One beta-glucanase unit (BGU) is defined as that quantity of enzyme that will liberate one micromole of reducing sugar (as glucose equivalents) per minute under the conditions of the assay.

c. Assay For Hemicellulase

Hemicellulase was assayed as described in *Food Chemicals Codex* 490-91, which is incorporated herein by reference. Briefly, the assay is based on the hydrolysis of the interior glucosidic bonds of a defined locust (carob) bean gum substrate at pH 40° C. The reduction in substrate viscosity is determined with a calibrated viscometer. One unit of hemicellulase activity (HCU) is that quantity of enzyme that will produce a relative fluidity change of 1.0 over a period of five minutes under the conditions of the assay.

d. Assay For Pectinase

Polygalacturonase activity was assayed by reacting polygalacturonic acid with $Na_3HPO_4$. Next, the sodium polygalacturonate produced by this reaction was mixed with a material containing polygalacturonase in a citric acid buffer, pH 3.0. The enzymatic reaction was allowed to proceed for 30 minutes at 20° C. The reduction in substrate viscosity was determined using a kinematic viscometer calibrated to read from 7-35 centipoises. One hundred units of polygalacturonase activity (PGU) is that quantity of enzyme that gives a 60%. reduction of viscosity in 30 minutes under the assay conditions.

e. Assay For Protease

Proteases from bacterial sources were assayed as described in *Food Chemicals Codex* 495-96, which is incorporated herein by reference. Briefly, the assay is based on a 30-minute hydrolysis of casein at 37° C., pH 7.0. Unhydrolized casein is removed by filtration, and the solubilized casein is determined spectrophotometrically. One bacterial protease unit (PC) is defined as that quantity of enzyme that produces the equivalent of 1.5 ug per ml of L-tyrosine per minute under the conditions of the assay.

Proteases from fungal sources were assayed as described in *Food Chemical Codex* 496-97, which is incorporated herein by reference. Briefly, the assay is based on a 30-minute hydrolysis of hemoglobin at pH 4.7. Unhydrolized hemoglobin was precipitated with trichloroacetic acid and removed by filtration. The quantity of solubilized hemoglobin in the filtrate is determined spectrophotometrically. One protease unit (HUT) is defined as that quantity of enzyme that produces, in one minute, under the assay conditions, a hydrolysate whose absorbance at 275 nm is the same as that of a solution containing 1.10 micrograms per ml of tyrosine in 0.006N hydrochloric acid. Crude fermentation products, partially purified enzyme mixtures or purified enzymes are next blended to produce the grain conditioners of the invention.

Preparation of the Grain Conditioner

An enzymatic grain condition for use on easier-to-digest grains (such as corn and wheat) should contain a pectinase, a beta-glucanase, an amylase and a hemicellulase. Preferred are grain conditioners containing the following types and amounts of enzyme activities per gram of final grain conditioner:

| | |
|---|---|
| Polygalacturonase | 1150–1450 PGU |
| Beta-glucanase | 125–175 BGU |
| Alpha-amylase | 1000–1700 SKB |
| | and 2000–3000 BAU |
| Hemicellulase | at least 15 HCU |

An enzymatic grain conditioner which can be used on all grains (including hard-to-digest grains such as milo, barley, oats and rye) should contain a pectinase, a protease, a beta-glucanase and an amylase. Preferred are grain conditioners containing the following types and amounts of enzyme activities per gram of grain conditioner:

| | |
|---|---|
| Polygalacturonase | 1150–1450 PGU |
| Protease | 7000–10000 PC |
| | and 3000–4500 HU |
| Beta-glucanase | 125–175 BGU |
| Alpha-amylase | 1000–1700 SKB |
| | and 2000–3000 BAU |

Although all of the enzymes in each grain conditioner contribute to the efficacy of that grain conditioner, the polygalacturonase activity is particularly important. Thus, it is most preferable to prepare grain conditioners containing near the maximum amount (1450 PGU) of polygalacturonase activity. In addition, when treating barley, it is preferable to prepare grain conditioners containing near the maximum amount (175 BGU) of beta-glucanase activity.

When crude fermentation products or partially purified enzyme mixtures are used, the resultant grain conditioner will contain other types of depolymerizing pectic enzymes, pectinesterases and other enzymes which are produced by the microorganisms along with the measured enzymes and are present in the crude fermentation products or partially purified enzyme mixtures used to prepare the grain conditioner. It is not necessary to quantitate these enzymes; an adequate amount of these enzymes will be present in the grain conditioner if the measured activities are kept within the limits given above. Of course, the grain conditioner would be effective even without these additional enzymes, but their presence is preferable.

The enzymatic grain conditioners of the invention may be liquids or powders. A liquid grain conditioner must contain enzyme preservatives (such as propylene glycol or sodium chloride) in addition to the enzymes and may optionally contain other ingredients which are not harmful to animals and do not inhibit the enzymes. For instance, the grain conditioners may contain a Federal Drug Administration-approved, food-grade surfactant to improve the wetting characteristics of the grain conditioner.

A dry grain conditioner need not contain enzyme preservatives since it will be mixed with water just before contacting the grain with the grain conditioner. At the time of mixing the dry grain conditioner with water, a surfactant may also be added. The dry grain conditioners of the invention may also optionally contain other ingredients which are not harmful to animals and do not inhibit the enzymes.

EXAMPLE 14

The partially purified liquid enzyme mixtures produced by fermenting *B. subtilis, A. oryzae, A. niger* and *R. oryzae* as described above in Examples 1 and 4–6 were assayed for polygalacturonase, alpha-amylase, beta-glucanase and hemicellulase activity using the assays set forth above. Then the fermentation products were blended together and were combined with a surfactant (Polysorbate 80) and enzyme preservatives (propylene glycol and calcium chloride dihydrate) to produce a grain conditioner having the following composition:

56.6 grams Polysorbate 80

35.4 grams propylene glycol (feed grade)

34.0 grams water 1.42 grams calcium chloride dihydrate 42.5 grams of an enzyme blend containing appropriates amounts of the various partially purified fermentation products so that the final grain conditioner had the following types and amounts of enzyme activity per gram of final grain conditioner:

| | |
|---|---|
| Polygalacturonase | 1450 PGU |
| Beta-glucanase | 150 BGU |
| Alpha-amylase | 1350 SKB |
| | and 2500 BAU |
| Hemicellulase | 15 HCU |

In addition, the grain conditioner contained other types of depolymerizing pectic enzymes, pectinesterases and other enzymes which were produced by the microorganisms along with the measured enzymes and were present in the partially purified enzyme mixtures used to prepare the grain conditioner.

This liquid grain conditioner will hereinafter be referred to as Grain Conditioner A-1. It is useful for treating easier-to-digest grains.

EXAMPLE 15

Another liquid grain conditioner having the formulation given in Example 14 is prepared using the partially purified fermentation products produced in Examples 7–9 and 12.

EXAMPLE 16

A dry grain conditioner having the formulation described in Example 14 is prepared using the partially purified fermentation products prepared as described in Example 13, except that no surfactant or preservative is included in the final grain conditioner.

EXAMPLE 17

Another liquid grain conditioner was prepared essentially as described in Example 14. The partially purified enzyme mixtures produced by fermenting *B. subtilis, A. oryzae, A. niger* and *R. oryzae* as described in Examples 1 and 4–6 were assayed for polygalacturonase, beta-glucanase, alpha-amylase and proteolytic activity as described above. The fermentation products were then blended together and were combined with a surfactant (Polysorbate 80) and enzyme preservatives (propylene glycol and calcium chloride dihydrate) to produce a grain conditioner having the following composition:

56.6 grams Polysorbate 80 (polyoxyethylene sorbitan mono-oleate)

35.4 grams propylene glycol (feed grade)

34.0 grams water 1.42 grams calcium chloride dihydrate 42.5 grams of an enzyme blend containing appropriate amounts of the various partially purified fermentation products so that the final grain conditioner had the following types and amounts of enzyme activity per gram of final grain conditioner:

| | |
|---|---|
| Polygalacturonase | 1450 PGU |
| Protease | 8500 PC |
| | and 3750 HU |
| Beta-glucanase | 150 BGU |
| Alpha-amylase | 1350 SKB |
| | and 2500 BAU |

This grain conditioner also contained other types of depolymerizing pectic enzymes, pectinesterases and other enzymes which were produced by the microorganisms along with the measured enzymes and were present in the partially purified enzyme mixtures used to prepare the grain conditioner.

This liquid grain conditioner will hereinafter be referred to as Grain Conditioner B-1. It is suitable for use on any grain, including hard-to-digest grains.

EXAMPLE 18

Another liquid grain conditioner is prepared having the formulation described in Example 17 using the partially purified fermentation products produced in Examples 7–9 and 12.

EXAMPLE 19

A dry grain conditioner is prepared having the formulation described in Example 17 using the partially purified fermentation products produced as described in Example 13, except that no surfactant or preservative is included in the final grain conditioner.

Treatment of Grain With Grain Conditioner

The enzymatic grain conditioners of the invention may be used to treat whole grain or may be used in combination with any other processing techniques. The grain conditioners of the invention are simply brought into contact with the grain and incubated with the grain for at least about 30 minutes. Thirty minutes is about the minimum time required to transport grain from processing equipment to the feeders, and generally no additional incubation time is necessary other than the time it takes to transport the processed grain to the feeders. When whole grain is used, a longer incubation (generally about 2–3 hours) is necessary. Of course, a longer incubation can be used even with processed grain, if desired. Some of the ways in which the grain conditioners can be used are the following.

1. Mechanical Scarification

This technique was generally described in the background section. The grain conditioners of the invention are applied in liquid form after the scarification of the grain is complete. An applicator system is used to accurately meter the flow of the grain conditioner onto a flow of the grain as it is being moved from the scarifying equipment to the feeders. The grain conditioner should be diluted with the smallest quantity of water that allows for good coverage of the grain. The water may be heated to assist in coverage and penetration of the grain conditioner into the grain, but temperatures should never exceed the temperature at which the least thermostable enzyme will be denatured (generally less than about 85° C.). The grain and grain conditioner are incubated together for the time it takes the grain to be transported from the scarifying equipment to the feeders (approximately 30 minutes). Additional incubation time may be used if desired.

2. Grinding and Rolling

Grains may be ground by passing them through a hammermill. Grain is rolled by passing it between two rollers. The grain may be rolled while it is dry (dry rolling) or the grain may be treated with a conventional grain conditioner (containing a surfactant, acid or base) and water prior to rolling to increase the moisture level of the grain (preconditioned rolled grain).

Also, the grain can be subjected to steam before being rolled. For instance, grain can be treated in a steam chamber at about 65°–85° C. for about 5–10 minutes before rolling (steam rolled grain) or can be treated in a steam chamber at about 90°–105° C. for about 20–30 minutes before being rolled into flakes (steam flaked grain). Grains are often treated with conventional grain conditioners prior to steam rolling and steam flaking to assist in moisture and heat penetration.

The rolled or ground grain is treated with the enzymatic grain conditioners of the invention after grinding or rolling. A liquid enzymatic grain conditioner or a dry grain conditioner dissolved in water may be applied and incubated with the grain as described above for mechanically scarified grain. The temperature of the grain when the enzymatic grain conditioner is applied should not exceed about 85° C. Ground grains treated with an enzymatic grain conditioner of the invention may also subsequently be pelleted to form an animal feed.

3. Soaking

Grain, whole or processed, may be soaked in water to increase the moisture level, preferably to 20% or greater and most preferably to 28–30%. For instance, whole grain or scarified grain can be soaked in water for a period of 12–24 hours. While soaking, the grains can be treated with the enzymatic grain conditioners of the invention by adding the grain conditioner (dry or wet) to the water in which the grain is soaked. Soaked whole grain can be fed immediately to animals, can be processed after soaking (generally by rolling) or can be stored in airtight containers for periods up to 21 days before being fed. Also, whole grain can be soaked in water, processed (such as by rolling), treated with the enzymatic grain conditioners of the invention and then fed.

4. Popped or Exploded

Grains can be exposed to radiant heat or super-heated air for very short times (10–20 seconds) which causes the grain to pop or explode. A liquid enzymatic grain conditioner is then applied to and incubated with the popped or exploded grain as described above for mechanical scarification.

5. Chemical Scarification

Grain can be chemically scarified with a conventional acid-type or base-type grain conditioner in the conventional manner. An enzymatic grain conditioner of the invention is then applied to and incubated with the chemically-scarified grain as described above for mechanical scarification.

6. High Moisture Grains

High moisture grains are grains harvested at higher than normal moisture levels. These grains are ground or rolled and then treated with the grain conditioners of the invention as described above for mechanical scarification. Finally, the grain is stored in pits or silos until needed.

EXAMPLE 20

Corn was dry rolled. After rolling, one batch of the corn was used as a control, one batch was treated with 6 ounces per ton (187 grams per metric ton) of Grain Conditioner A-1, one batch was treated with 9 ounces per ton (281 grams per metric ton) of Grain Conditioner A-1 and one batch was treated with 6 ounces per ton (187 grams per metric ton) of E-Z FLAKE 4. Another batch of corn was treated with 6 ounces per ton (187 grams per metric ton) of E-Z FLAKE 4 before dry rolling and with 3 ounces per ton (93.5 grams per metric ton) of Grain Conditioner A-1 after rolling.

E-Z FLAKE 4 is a conventional acid-type grain conditioner comprising 35–45% propionic acid and lecithin. It is manufactured by Loveland Industries, Greeley, Colo.

The E-Z FLAKE 4 and Grain Conditioner A-1 were diluted with enough water to provide good coverage of the grain and to achieve the degree of added moisture set forth in Table 1. When the corn was treated with E-Z FLAKE 4, it was incubated with the E-Z FLAKE 4 for about 2–3 hours. The corn was incubated with Grain Conditioner A-1 also for about 2–3 hours.

After treatment with E-Z FLAKE 4 and/or Grain Conditioner A-1, the treated and control corn was dried in an oven at 100° C. for 12 hours. After drying, the corn was ground in a mill fitted with a 0.8 mm screen.

The in vitro dry matter digestibility of both control and treated corn was determined by a modified Tilley and Terry procedure as follows. First, 0.5 g of either the dried and ground corn, control or treated, either was placed in a centrifuge tube. Then, a mixture of 10 ml of rumen liquor (taken from a fistulated sheep and strained through four layers of muslin cloth) and 40 ml McDougall's buffer was put into each tube. McDougall's buffer contains 49 g. $NaHCO_3$, 18.6 g $Na_2HPO_4$, 100 ml of a solution of 28.5 g KCl, 23.5 g NaCl, 6 g $MgCl_2.7H_2O$ and 2 g CaCl per liter and enough water to bring the total volume of the buffer to 1000 ml. The dispenser was fitted with a tube through which $CO_2$ was passed continuously, so as to displace air from the tube, thus maintaining anaerobic conditions. The tubes were stoppered with rubber bungs fitted with gas release valves, and then placed in an incubator at 38° C. for 48 hours. The tubes were shaken gently twice daily. One blank tube, containing only rumen liquor and buffer, and two tubes containing standard samples of known digestibility were included in the test. The pH during incubation was kept between the limits of 6.7 to 6.9.

After 48 hours, the tubes were cooled by immersion in cold water. Occasional shaking at this stage helped settle the particulate matter. The tubes were centrifuged at 2500 revolutions per minute for 10 minutes after which the supernatant was poured off. Then, 50 ml of acid pepsin (0.2% solution in 0.1N HCl) was added and the residue broken up with a metal spatula. After a further 48 hour incubation at 38° C., again with twice daily shaking, the tubes were centrifuged, the supernatant poured off and the residue transferred to a weighed alumina crucible with the minimum of water.

The crucibles plus residues were dried overnight at 100° C., cooled in desiccators and weighed. The organic matter residues were obtained after ashing the crucibles plus residue overnight.

The results are presented in Table 1. Treatment of corn with Grain Conditioner A-1 at 6 ounces per ton (Group 4) gave the greatest improvement compared to untreated dry rolled corn (control) in the dry matter digestibility for all of the treatments as evidenced particularly by the 48-hour readings.

TABLE 1

| GRAIN AND TREATMENT | DRY MATTER DIGESTIBILITY (% digested) | | | | |
|---|---|---|---|---|---|
| | 4 h | 8 h | 16 h | 48 h | 96 h |
| CORN | | | | | |
| 1. Control (untreated) | 18.4 | 36.2 | 80.1 | 87.1 | 91.9 |
| 2. E-Z FLAKE 4 (6 oz/ton) with 3% added moisture | 18.1 | 37.5 | 81.6 | 87.8 | 92.0 |
| 3. E-Z FLAKE 4 (6 oz/ton) + 1½% added moisture before rolling; Grain Conditioner A-1 (3 oz/ton) with 4% added moisture after rolling | 11.7 | 33.1 | 85.0 | 87.7 | 92.8 |
| 4. Grain Conditioner A-1 (6 oz/ton) with 3% added moisture | 16.9 | 42.0 | 82.4 | 91.6 | 91.6 |
| 5. Grain Conditioner A-1 (9 oz/ton) with 3% added moisture | 12.5 | 39.6 | 87.1 | 82.2 | 91.9 |
| MILO | | | | | |
| 1. Control (untreated) | 19.5 | 39.4 | 81.2 | 79.3 | 89.7 |
| 2. Grain Conditioner B-1 (6 oz/ton) | 14.6 | 49.9 | 81.4 | 80.6 | 85.7 |
| 3. Grain Conditioner B-1 (12 oz/ton) | 18.0 | 45.9 | 81.3 | 87.1 | 87.1 |
| BARLEY | | | | | |
| 1. Control (untreated) | 22.0 | 47.0 | 69.9 | 81.4 | 82.8 |
| 2. Grain Conditioner B-1 (6 oz/ton) | 25.0 | 54.5 | 84.0 | 77.3 | 85.7 |
| 3. Grain Conditioner B-1 (12 oz/ton) | 25.1 | 55.2 | 82.2 | 85.7 | 83.8 |

EXAMPLE 21

The method of Example 20 was repeated, except that dry rolled milo and Grain Conditioner B-1 were used. The treatments and results are also shown in Table 1. Milo treated with 9 ounces per ton of Grain Conditioner B-1 showed improved dry matter digestibility as compared to untreated dry rolled milo (control), and milo treated with 6 ounces per ton of Grain Conditioner B-1 gave slightly improved dry matter digestibility.

EXAMPLE 22

The method of Example 21 was repeated using dry rolled barley as the grain. The results are shown in Table 1. These data show that treatment with Grain Conditioner B-1 at both doses improves dry matter digestibility, especially at higher levels of application, compared to untreated dry rolled barley (control).

EXAMPLE 23

Corn was treated with enzymatic Grain Conditioner A-1 and E-Z FLAKE 4 as described in Example 20. In vitro gas production was measured by placing a 0.8 g sample of the control or treated corn, 0.5 g commercial Baker's Yeast and 10 ml of a 0.2% (weight/volume) amyloglucosidase enzyme solution into a 5 ml flask connected to an inverted cylinder. This mixture was incubated at 102.2° F., and gas measurements were determined by water displacement. Readings were taken at 0, 2, 4 and 8 hours.

The results are shown in Table 2. As can be seen there, treating the dry rolled corn with Grain Conditioner A-1 or E-Z FLAKE 4 increased in vitro gas production. The best results were obtained with 6 ounces of Grain Conditioner B-1 per ton of corn. Improved in vitro gas production is evidence of improved carbohydrate availability.

TABLE 2

| GRAIN AND TREATMENT | GAS PRODUCTION (mg/g) | | | % average change |
|---|---|---|---|---|
| | 2 h | 4 h | 8 h | |
| CORN | | | | |
| 1. Control | 12.46 | 16.00 | 18.29 | — |
| 2. E-Z FLAKE 4 (6 oz/ton) with 3% added moisture | 13.64 | 22.40 | 25.58 | +31 |
| 3. E-Z FLAKE 4 (6 oz/ton) + 1½% added moisture before rolling; Grain Conditioner A-1 (3 oz/ton) with 4% added moisture after rolling | 16.39 | 25.15 | 28.33 | +49 |
| 4. Grain Conditioner A-1 (6 oz/ton) with 3% added moisture | 18.90 | 28.66 | 34.66 | +76 |
| 5. Grain Conditioner A-1 (9 oz/ton) with 3% added moisture | 20.22 | 18.61 | 17.99 | +22 |
| MILO | | | | |
| 1. Control | 22.40 | 30.15 | 33.83 | — |
| 2. Grain Conditioner B-1 (6 oz/ton) | 19.60 | 28.58 | 32.55 | −6.5 |
| 3. Grain Conditioner A-1 (12 oz/ton) | 17.35 | 26.10 | 33.23 | −11 |
| BARLEY | | | | |
| 1. Control | 21.78 | 28.38 | 34.16 | — |
| 2. Grain Conditioner B-1 (6 oz/ton) | 21.60 | 31.25 | 40.14 | +10 |
| 3. Grain Conditioner B-1 (12 oz/ton) | 19.31 | 26.50 | 32.48 | −7 |

EXAMPLE 24

Dry rolled milo was treated with Grain Conditioner B-1 as described in Example 21. In vitro gas production was measured as described in Example 23.

The results are also shown in Table 2. As can be seen from Table 2, treatment with Grain Conditioner B-1 slightly depressed in vitro gas production as compared to untreated dry rolled milo (control).

EXAMPLE 25

Dry rolled barley was treated with Grain Conditioner B-1 as described in Example 22. In vitro gas production was measured as described in Example 23.

The results are shown in Table 2. As can be seen, the use of 6 ounces of Grain Conditioner B-1 per ton of barley slightly increased in vitro gas production as compared to untreated dry rolled barley (control), while the use of 12 ounces of Grain Conditioner B-1 per ton slightly depressed in vitro gas production.

EXAMPLE 26

Six groups of 10 rats each, individually penned, were fed feeds comprising either steam flaked milo or barley which was either treated or untreated with Grain Conditioner B-1. Also, two different levels of Grain Conditioner B-1 were used.

Grain Conditioner B-1 was added to the grain with enough water to allow for good coverage of the grain. The steam flaked milo or barley was then incubated with Grain Conditioner B-1 for about 1–2 hours.

The milo and barley, treated and untreated, were formulated into a Nutritional Research Council (NRC) minimal diet for rats using the grain as the base and soybean meal to balance protein requirements. The rats were fed ad libitum and were weighed immediately before the test began and 21 days later.

The results are shown in Table 3. As can be seen there, diets containing milo treated with 6 ounces Grain Conditioner A-1 per ton gave improved weight gains (15%) and feed utilization efficiency (12%). Diets containing milo treated with 12 ounces per ton of Grain Conditioner B-1 also gave improved performance, but the improvement was not as great as for the lower level of Grain Conditioner B-1.

The results were reversed for barley. The higher level of Grain Conditioner B-1 gave a greater improvement in weight gain (7%) and feed utilization (10%) than did the lower level of Grain Conditioner B-1 (2% improvement in weight gain and 1% improvement in feed utilization efficiency).

TABLE 3

| Grain | Treatment | Feed Consumed per rat per day (g) | Weight Gain per rat per day (g) | Gain:Feed Ratio |
|---|---|---|---|---|
| Milo | Control (Steam Flaked only) | 14.9 | 3.80 | 0.255 |
| | 6 oz/ton Grain Conditioner B-1 | 15.3 | 4.37 (+15%) | 0.286 (+12%) |
| | 12 oz/ton Grain Conditioner B-1 | 15.0 | 3.98 (+5%) | 0.265 (+4%) |
| Barley | Control (Steam Flaked only) | 12.9 | 3.98 | 0.309 |
| | 6 oz/ton Grain Conditioner B-1 | 12.2 | 4.06 (+2%) | 0.333 (+7%) |
| | 12 oz/ton Grain Conditioner B-1 | 12.4 | 4.27 (+7%) | 0.344 (+10%) |

EXAMPLE 27

Another rat growth study was performed essentially as described in Example 26 using a barley-based diet. Eight groups of 10 rats were fed NRC diets containing dry rolled barley treated as follows:

| Group | Grain | Treatment |
|---|---|---|
| A | Barley | Untreated |
| B | Barley | 7 oz/ton (218 g/metric ton) E-Z FLAKE 4; 4–5% added H₂O |
| C | Barley | 1.76 oz/ton (55 g/metric ton) Grain Conditioner B-1; 3.5% added H₂O |
| D | Barley | 10.3 oz/ton (322 g/metric ton) Grain Conditioner B-1; 3.5% added H₂O |
| E | Barley | 7 oz/ton (218 g/metric ton) E-Z FLAKE 4; 4.44 oz/ton (139 g/metric ton) Grain Conditioner B-1; 7.5% added H₂O |
| F | Barley | 7 oz/ton (218 g/metric ton) E-Z FLAKE 4; 9.23 oz/ton (289 g/metric ton) Grain Conditioner B-1; 7.5% added H₂O |
| G | Wheat | Untreated |

The barley was dry rolled. The rolled barley was incubated with Grain Conditioner B-1 for about 1–2 hours. When E-Z FLAKE 4 was used, it was applied before rolling, and the whole grain was incubated with the E-Z FLAKE 4 for about 1–2 hours. The wheat was cracked but otherwise untreated.

The results are shown in Table 4. As can be seen there, Grain Conditioner B-1 alone at 10.3 ounces per ton (Group D) gave excellent improvement in weight gain and feed utilization efficiency compared to untreated dry rolled barley (Group A). E-Z FLAKE 4 alone (Group B) also gave comparable results, but using both sequentially (Groups E and F) was not as effective in this study as using either one alone. The weight gains and feed utilization obtained with Grain Conditioner B-1 and E-Z FLAKE 4 individually were comparable to those obtained for untreated cracked wheat.

TABLE 4

| Group | Average Daily Feed Consumption Per Rat (g) | Ave. Daily Wt. Gain Per Rat (g) | Feed:Gain Ratio |
|---|---|---|---|
| A | 21.7 | 2.50 | 8.68 |
| B | 22.9 | 3.29 (+32%) | 6.96 (−20%) |
| C | 22.9 | 2.61 (+4%) | 8.77 (+1%) |
| D | 20.0 | 3.00 (+20%) | 6.67 (−23%) |
| E | 20.7 | 2.72 (+9%) | 7.61 (−12%) |
| F | 23.3 | 2.78 (+11%) | 8.38 (−3%) |
| G | 22.2 | 3.19 (+28%) | 6.96 (−20%) |

EXAMPLE 30

Sixteen batches of whole milo were treated as follows:

| | | Treatment | | |
|---|---|---|---|---|
| Batch | Moisture Level of Milo | Scarified | Rolled | Grain Conditioner B-1* |
| 1 | 12.5% | No | No | No |
| 2 | 12.5% | No | No | Yes |
| 3 | 12.5% | No | Yes | No |
| 4 | 12.5% | No | Yes | Yes |
| 5 | 12.5% | Yes | No | No |
| 6 | 12.5% | Yes | No | Yes |
| 7 | 12.5% | Yes | Yes | No |
| 8 | 12.5% | Yes | Yes | Yes |

-continued

| Batch | Moisture Level of Milo | Treatment Scarified | Rolled | Grain Conditioner B-1* |
|---|---|---|---|---|
| 9 | 17.5% | No | No | No |
| 10 | 17.5% | No | No | Yes |
| 11 | 17.5% | No | Yes | No |
| 12 | 17.5% | No | Yes | Yes |
| 13 | 17.5% | Yes | No | No |
| 14 | 17.5% | Yes | No | Yes |
| 15 | 17.5% | Yes | Yes | No |
| 16 | 17.5% | Yes | Yes | Yes |

*Grain Conditioner B-1 was used at 6 ounces per ton milo (187 grams per metric ton), and was added with enough water to get good coverage of the grain. The grain conditioner was incubated with whole, scarified or scarified plus rolled milo for 0.5–1.0 hour at 25° C.

Also, two batches (17 and 18) of milo were steam flaked. Batch 17 was not treated further, while Batch 18 was incubated with 6 ounces per ton (187 grams per metric ton) of Grain Conditioner B-1 and enough water to get good coverage of the grain for about 1.0 hour.

The content of reducing sugar in milligrams of maltose equivalents per gram of grain was measured for each batch of milo as follows. Five gram samples were taken from each batch of grain and were vigorously extracted with 40 ml distilled water per 5 g sample at 4° C. for 60 minutes. The extracts were filtered through Whatman No. 1 filter paper. Then, 1.0 ml of each filtrate was mixed with an equal volume of a 1% solution of 3,5-dinitrosalicylic acid in 0.4N NaOH with 30% sodium potassium tartrate, and the mixture was heated in a boiling water bath for 5 minutes. The resultant solution was diluted 1:5 with distilled water, and the absorbance of the diluted solution was read at 540 nm. The concentration of reducing sugar in maltose equivalents was determined by comparison of the absorbance of the experimental solutions to the absorbance of a series of solutions of known maltose concentration.

The results are shown in Table 5. As can be seen there, treatment with Grain Conditioner B-1 generally increased the content of maltose equivalents compared to milo processed in the same way but not treated with Grain Conditioner B-1 (except for Batches 6 and 10). These results show that the use of the enzymatic grain conditioners of the invention generally increase carbohydrate availability.

TABLE 5

| Batch | Sugar Content (Mg. Maltose Equivalents Per Gram of Grain) | % Increase With Enzyme |
|---|---|---|
| 1 | 2.0 | — |
| 2 | 2.32 | +16% |
| 3 | 9.6 | — |
| 4 | 10.8 | +12.5 |
| 5 | 2.0 | — |
| 6 | 2.0 | 0 |
| 7 | 10.0 | — |
| 8 | 13.6 | +36% |
| 9 | 1.3 | — |
| 10 | 1.12 | −14% |
| 11 | 7.6 | — |
| 12 | 11.5 | +51% |
| 13 | 0.5 | — |
| 14 | 0.96 | +92% |

TABLE 5-continued

| Batch | Sugar Content (Mg. Maltose Equivalents Per Gram of Grain) | % Increase With Enzyme |
|---|---|---|
| 15 | 8.0 | — |
| 16 | 11.2 | +40% |
| 17 | 3.6 | — |
| 18 | 6.2 | 72% |

EXAMPLE 31

Several different types of grain were treated with the grain conditioners of the invention, and maltose equivalents were measured as described in Example 30. Treatment of the grain was as follows:

| Batch | Grain | Treatment Processing Cracked | Scarified | Grain Conditioner* |
|---|---|---|---|---|
| 1 | Wheat | + | — | — |
| 2 | Wheat | + | — | + |
| 3 | Wheat | — | + | — |
| 4 | Wheat | — | + | + |
| 5 | Oats | + | — | — |
| 6 | Oats | + | — | + |
| 7 | Oats | — | + | — |
| 8 | Oats | — | + | + |
| 9 | Barley | + | — | — |
| 10 | Barley | + | — | + |
| 11 | Barley | — | + | — |
| 12 | Barley | — | + | + |

*Grain Conditioner B-1 was used to treat the barley and oats, and Grain Conditioner A-1 was used to treat the wheat. Both grain conditioners were used at 6 ounces per ton (187 grams per metric ton) and were added with enough water to get good coverage of the grain. The cracked or scarified grain was incubated with the grain conditioner for about 1.0 hour.

The results are shown in Table 7. As can be seen, treatment with the grain conditioners of the invention increased the sugar content (in maltose equivalents) of all grains, whether cracked or scarified. The greatest increases were seen for scarified wheat and cracked barley. Thus, treatment with the grain conditioners of the invention improved carbohydrate availability.

TABLE 7

| Batch | Sugar Content (mg. maltose equivalents per gram grain) | % Increase with Enzyme Treatment Compared To Untreated |
|---|---|---|
| 1 | 17.3 | — |
| 2 | 20.3 | +17.3 |
| 3 | 4.8 | — |
| 4 | 8.3 | +72.9 |
| 5 | 8.7 | — |
| 6 | 10.1 | +16.1 |
| 7 | 7.2 | — |
| 8 | 9.4 | +30.6 |
| 9 | 6.8 | — |
| 10 | 11.9 | +75.0 |
| 11 | 6.0 | — |
| 12 | 6.2 | +20.0 |

EXAMPLE 32

Several batches of whole milo were treated as follows:

| Batch | Treatment | | | |
|---|---|---|---|---|
| | None (Whole) | Cracked | Steam Rolled | Grain Conditioner B-1* |
| 1 | X | | | |
| 2 | X | | | X |
| 3 | | X | | |
| 4 | | X | | X |
| 5 | | | X | |
| 6 | | | X | X |

*Grain Conditioner was used B-1 at 6 ounces per ton (187 grams per metric ton) of milo. The grain conditioner was incubated with the whole, cracked or steam rolled milo for about 1.0 hour in the presence of enough water to obtain good coverage of the grain.

Then, the content of reducing sugar was measured as described in Example 30, except that the standard solutions contained known concentrations of dextrose. Thus, the sugar content is expressed in dextrose equivalents. The results are shown in Table 6. Treatment with Grain Conditioner B-1 increased the sugar content of the milo (in dextrose equivalents) for all processing conditions tested, showing that the use of the enzymatic grain conditioners of the invention improved carbohydrate availability.

TABLE 6

| Group | Sugar Content (Mg. Dextrose Equivalents Per Gram Grain) | % Increase With Enzyme Compared to Untreated |
|---|---|---|
| 1 | 2.9 | — |
| 2 | 3.25 | +12% |
| 3 | 4.3 | — |
| 4 | 6.1 | +42% |
| 5 | 4.8 | — |
| 6 | 8.5 | +77% |

We claim:

1. A method of increasing the weight gain and feed utilization efficiency of an animal comprising the steps of:
   providing a grain conditioner comprising:
   a pectinase,
   a protease,
   a beta-glucanase,
   an amylase, and
   a non-ionic, food grade surfactant;
   applying the grain conditioner to grain sorghum; and
   feeding the animal the conditioned grain sorghum.

2. The method of claim 1 wherein the surfactant is polyoxyethylene sorbitan mono-oleate.

3. The method of claim 1 wherein the pectinase includes a polygalacturonase and the grain conditioner comprises per gram from about 1150 to about 1450 PGU of the polygalacturonase, from about 7000 to about 10000 PC of a bacterial protease, from about 3000 to about 4500 HU of a fungal protease, from about 125 to about 4500 HU of a fungal protease, from about 125 to about 75 BGU of beta-glucanase, from about 2000 to about 3000 BAU of a bacterial alpha-amylase and from about 1000 to about 1700 SKB of a fungal alpha-amylase.

4. The method of claim 3 wherein the surfactant is polyoxyethylene sorbitan mono-oleate.

5. The method of claim 4 further including the step of:
   allowing the grain conditioner to condition the grain sorghum for at least 30 minutes prior to the feeding step.

6. A method of increasing the weight gain and feed utilization efficiency of an animal comprising the steps of:
   providing a grain conditioner which comprises a pectinase, a beta-glucanase, an amylase, a hemicellulase and a non-ionic, food grade surfactant;
   applying the grain conditioner to an easier-to-digest grain; and
   feeding the conditioned easier-to-digest grain to the animal.

7. The method of claim 6 wherein the surfactant is polyoxyethylene sorbitan mono-oleate.

8. The method of claim 6 wherein the pectinase includes a polygalacturonase and the grain conditioner comprises per gram from about 1150 to about 1450 PGU of the polygalacturonase, from about 125 to about 175 BGU of a beta-glucanase, from about 2000 to about 3000 BAU of a bacterial alpha-amylase, from about 1000 to about 1700 SKB of a fungal alpha-amylase and at least about 15 HCU of a hemicellulase.

9. The method of claim 8 wherein the surfactant is polyoxyethylene sorbitan mono-oleate.

10. The method of claim 9 further including the step of:
    allowing the grain conditioner to condition the grain for at least 30 minutes prior to the feeding step.

11. The method of claim 1 further including the step of:
    treating the grain sorghum by a method selected from the group consisting of mechanical scarification, chemical scarification, milling, grinding, rolling, exploding and popping.

12. The method of claim 11 wherein the pectinase includes an endo-pectinase and an exo-pectinase.

13. The method of claim 11 wherein the protease includes a bacterial protease and a fungal protease.

14. The method of claim 11 wherein the amylase includes a bacterial alpha-amylase and a fungal alpha-amylase.

15. The method of claim 11 wherein the pectinase includes a polygalacturonase.

16. The method of claim 11 wherein the pectinase includes a polygalacturonase, the protease includes a bacterial protease and a fungal protease, and the amylase includes a bacterial alpha-amylase and a fungal alpha-amylase.

17. The method of claim 1 further including the step of:
    allowing the grain conditioner to condition the grain sorghum for at least 30 minutes prior to the feeding step.

18. The method of claim 17 wherein the pectinase includes a polygalacturonase.

19. The method of claim 18 further including the step of:
    treating the grain sorghum by a method selected from the group consisting of mechanical scarification, chemical scarification, milling, grinding and popping.

20. The method of claim 19 wherein the grain treating step is performed before the grain conditioner application step.

* * * * *